(12) United States Patent
Nakamura (10) Patent No.: US 10,365,324 B2
(45) Date of Patent: Jul. 30, 2019

(54) ANALYSIS SYSTEM AND ANALYSIS METHOD

(71) Applicant: HAMAMATSU PHOTONICS K.K., Hamamatsu-shi, Shizuoka (JP)

(72) Inventor: Tomonori Nakamura, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 173 days.

(21) Appl. No.: 15/515,686

(22) PCT Filed: Oct. 9, 2014

(86) PCT No.: PCT/JP2014/077098
§ 371 (c)(1),
(2) Date: Mar. 30, 2017

(87) PCT Pub. No.: WO2016/056109
PCT Pub. Date: Apr. 14, 2016

(65) Prior Publication Data
US 2017/0307682 A1    Oct. 26, 2017

(51) Int. Cl.
*G01J 5/00* (2006.01)
*G01K 1/00* (2006.01)
*G01N 25/00* (2006.01)
*G01R 31/311* (2006.01)
*G01N 25/72* (2006.01)
*G01R 31/26* (2014.01)
*G01K 17/08* (2006.01)
(Continued)

(52) U.S. Cl.
CPC .......... *G01R 31/311* (2013.01); *G01J 5/0003* (2013.01); *G01J 5/0007* (2013.01); *G01J 5/0066* (2013.01); *G01K 17/08* (2013.01);
*G01K 17/16* (2013.01); *G01N 21/88* (2013.01); *G01N 25/005* (2013.01); *G01N 25/20* (2013.01); *G01N 25/72* (2013.01); *G01R 31/26* (2013.01)

(58) Field of Classification Search
USPC .......................................... 374/120, 121, 45
See application file for complete search history.

(56) References Cited

U.S. PATENT DOCUMENTS 5,089,700 A    2/1992   Sapia et al.
6,146,014 A    11/2000  Bruce et al.
(Continued)

FOREIGN PATENT DOCUMENTS

AU           538602      8/1984
JP           S63-134943 A   6/1988
(Continued)

OTHER PUBLICATIONS

International Preliminary Report on Patentability dated Apr. 20, 2017 for PCT/JP2014/077098.

*Primary Examiner* — Mirellys Jagan
(74) *Attorney, Agent, or Firm* — Drinker Biddle & Reath LLP (57) ABSTRACT

A system and a method capable of identifying a heat source position corresponding to a failure portion are provided. An analysis system according to the present invention is an analysis system that identifies a heat source position inside a semiconductor device, and includes a tester that applies an AC signal to the semiconductor device, an infrared camera that detects light from the semiconductor device according to the AC signal and outputs a detection signal, and a data analysis unit that identifies the heat source position based on the detection signal.

12 Claims, 7 Drawing Sheets

(51) Int. Cl.
*G01K 17/16* (2006.01)
*G01N 21/88* (2006.01)
*G01N 25/20* (2006.01)

(56) References Cited

U.S. PATENT DOCUMENTS

2010/0062550 A1 3/2010 Buchel et al.
2011/0142091 A1 6/2011 Wardle et al.

FOREIGN PATENT DOCUMENTS

| JP | H04-249336 A | 9/1992 |
| JP | H09-266238 A | 10/1997 |
| JP | 2013-526723 A | 6/2013 |
| WO | WO-2011/156527 A1 | 12/2011 |

ANALYSIS SYSTEM AND ANALYSIS METHOD

TECHNICAL FIELD

The present invention relates to a system and a method of identifying a position of a heat source generated inside a measurement object.

BACKGROUND ART

In a related art, a system that analyzes a position of a heat source of a measurement object is known as a system that analyzes a failure portion of the measurement object (see, for example, Patent Literature 1). In the system of Patent Literature 1, a modulation current is applied to a measurement object, heat generated from a heat source inside the measurement object is detected by an infrared camera, and a position of the heat source (a failure portion) is analyzed by using the fact that the heat source is generated at the failure portion due to the application of a modulation current.

CITATION LIST

Patent Literature

[Patent Literature 1] Japanese Unexamined Patent Publication No. 2013-526723

SUMMARY OF INVENTION

Technical Problem

Here, in a case in which a plurality of types of metals are included in a measurement object, if a modulation current is applied to the measurement object, a transfer (absorption or emission) of heat occurs between the metals due to the Peltier effect. Accordingly, heat from a heat source is transferred to a position different from an actual failure portion, and a position of the heat source corresponding to the failure portion may not be identified with high accuracy.

Thus, an object of the present invention is to provide an analysis system and an analysis method capable of identifying a heat source position corresponding to a failure portion.

Solution to Problem

An analysis system according to the present invention is an analysis system that identifies a heat source position inside a measurement object, and includes an applying unit that applies an alternating current (AC) signal to the measurement object; a light detection unit that detects light from the measurement object according to the AC signal and outputs a detection signal; and an analysis unit that identifies the heat source position based on the detection signal.

An analysis method of the present invention is an analysis method of identifying a heat source position inside a measurement object, includes the steps of: applying an AC signal to the measurement object; detecting light from the measurement object according to the AC signal and outputting a detection signal; and identifying the heat source position based on the detection signal.

In the analysis system and the analysis method, the AC signal is applied to the measurement object, and light from the measurement object according to the AC signal is detected. If there is a failure portion in the measurement object, a modulation current is applied to the measurement object, and accordingly, a heat source is generated in the failure portion. If a portion in which the heat source is generated is near a bonding surface of different metals, a heat transfer is caused between the different metals by the Peltier effect, and heat from the heat source may be transferred to a position different from the failure portion. In this regard, in the present invention, since the AC signal is applied to the measurement object, a direction of the current applied to the measurement object periodically changes (changes to an opposite direction). More specifically, since the AC signal is adjusted so that the amounts of current flowing through both sides are equal to a reference voltage of a semiconductor device SD, an influence of the Peltier effect is canceled, and a situation in which heat from the heat source is transferred to a position different from a failure portion can be suppressed. Since the light from the measurement object changes according to the heat source position, it is possible to appropriately identify the heat source position corresponding to the failure portion by analyzing the heat source position based on the light.

Further, in the analysis system and the analysis method of the present invention, the AC signal may be applied according to a trigger signal with a predetermined lock-in cycle to apply the AC signal with an amplitude in an OFF period of the lock-in cycle that is smaller than in an ON period of the lock-in cycle. It is possible to appropriately perform a lock-in measurement by reducing the amplitude of the AC signal in the OFF period of the lock-in cycle.

Further, in the analysis system and the analysis method of the present invention, the amplitude of the AC signal may be set to 0 in the OFF period of the lock-in cycle. Thus, it is possible to more appropriately perform lock-in measurement.

Further, in the analysis system and the analysis method of the present invention, a phase of the AC signal may be changed every lock-in cycle so that the amplitude of the AC signal is canceled when AC signals with a plurality of lock-in cycles are integrated. Accordingly, it is possible to suppress a situation in which a result of analyzing the heat source position is influenced by the integrated AC signal.

Further, in the analysis system and the analysis method of the present invention, a frequency of the AC signal may be higher than a frequency of the trigger signal. By causing the frequency of the AC signal to be higher, a direction of the current applied to the measurement object is frequently changed, and it is possible to further suppress the situation in which the heat from the heat source is transferred by the Peltier effect.

Further, in the analysis system and the analysis method of the present invention, the heat source position may be identified by deriving a phase delay amount of the detection signal relative to the trigger signal. The phase delay amount of the detection signal relative to the trigger signal changes according to the light from the measurement object. Therefore, it is possible to identify the heat source position by deriving the phase delay amount of the detection signal. The derivation of the phase delay amount can be easily performed. Further, since the phase delay amount and the light from the measurement object have a close correspondence relationship, it is possible to identify the heat source position easily and with high accuracy by deriving the phase delay amount of the detection signal.

Further, in the analysis system of the present invention, the light detection unit may be an infrared camera that detects infrared rays from the heat source as the light from the measurement object. Using the infrared camera, it is possible to appropriately detect light (infrared light) with a simple configuration.

Further, the analysis system of the present invention may further include a setting unit that sets a measurement point for the measurement object; and a light irradiation unit that irradiates the measurement object with light, and the light detection unit may be a photodetector that detects light reflected from the measurement point according to the irradiation of the light from the light irradiation unit as the light from the measurement object. Using the photodetector, it is possible to improve time resolution and to perform identifying of the heat source position inside the measurement object with higher accuracy.

Advantageous Effects of Invention

According to the present invention, it is possible to provide an analysis system and an analysis method capable of analyzing a heat source position corresponding to a failure portion.

DESCRIPTION OF EMBODIMENTS

Hereinafter, preferred embodiments of the present invention will be described in detail with reference to the drawings. In respective figures, the same or corresponding portions are denoted with the same reference numerals, and repeated description will be omitted.

First Embodiment

Figure 1:
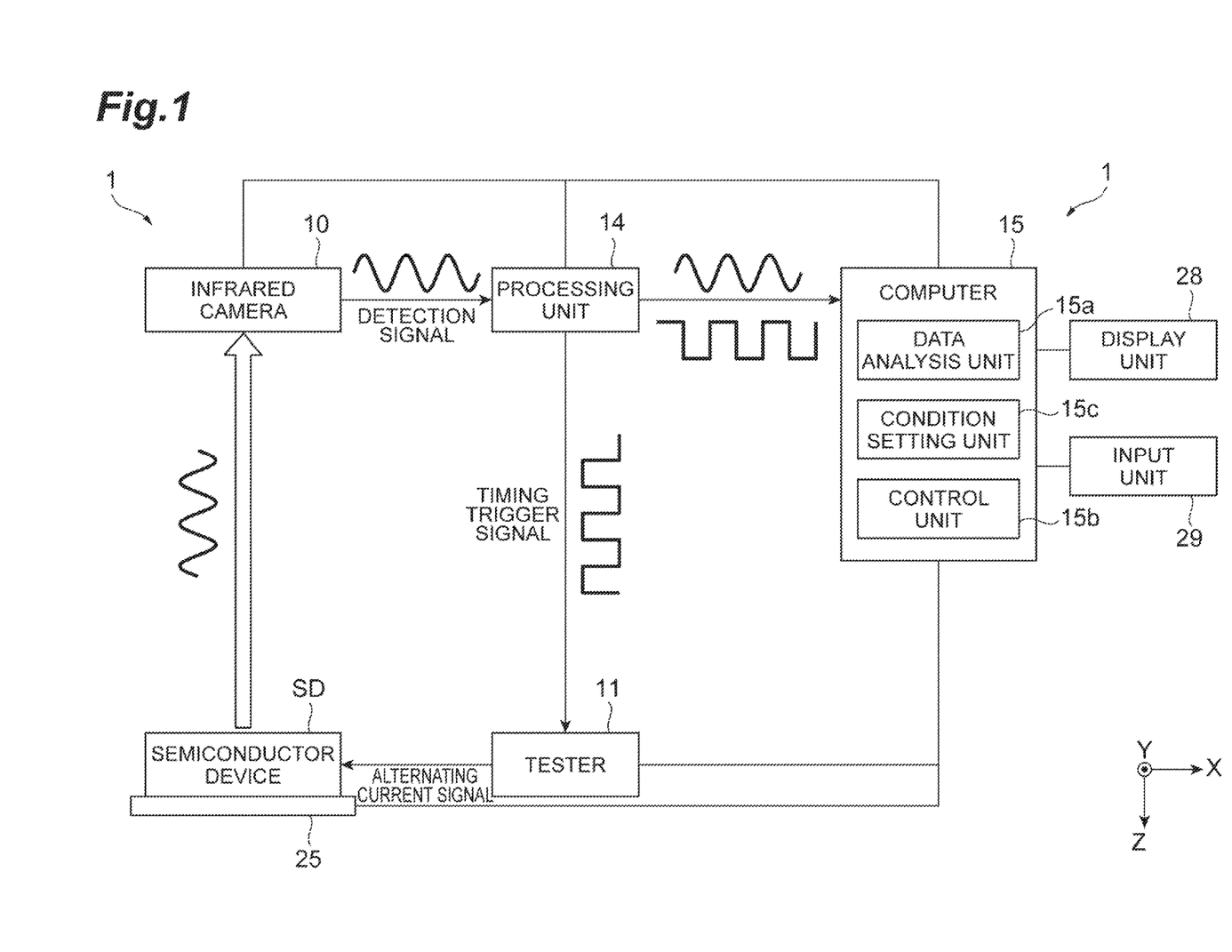
FIG. 1 is a configuration diagram of an analysis system according to a first embodiment of the present invention.

As illustrated in FIG. 1, an analysis system 1 according to a first embodiment is an analysis system that identifies a heat source position inside a semiconductor device SD (a measurement object), which is a device under test (DUT). A heat source is a heat generating portion inside the semiconductor device SD. If there is a short-circuited portion or the like inside the semiconductor device SD when a signal is applied to the semiconductor device SD, the short-circuited portion generates heat and becomes a heat source. That is, the analysis system 1 is a failure analysis system that analyzes an abnormality of the short-circuited portion or the like inside the semiconductor device SD by identifying a heat source position.

For example, an integrated circuit having a PN junction of a transistor or the like (for example, a small scale integration (SSI), a medium scale integration (MSI), a large scale integration (LSI), a very large scale integration (VLSI), an ultra large scale integration (VLSI), or a giga scale integration (GSI)), a MOS transistor and a bipolar transistor for large current/high voltage, or a memory storage device can be used as the device under test.

The analysis system 1 includes an infrared camera 10 (a light detection unit), a tester 11 (an applying unit), a processing unit 14, a computer 15, a display unit 28, and an input unit 29. The computer 15 includes a data analysis unit 15a (an analysis unit), a condition setting unit 15c (a setting unit), and a control unit 15b. The semiconductor device SD is placed on a stage 25.

Figure 2:
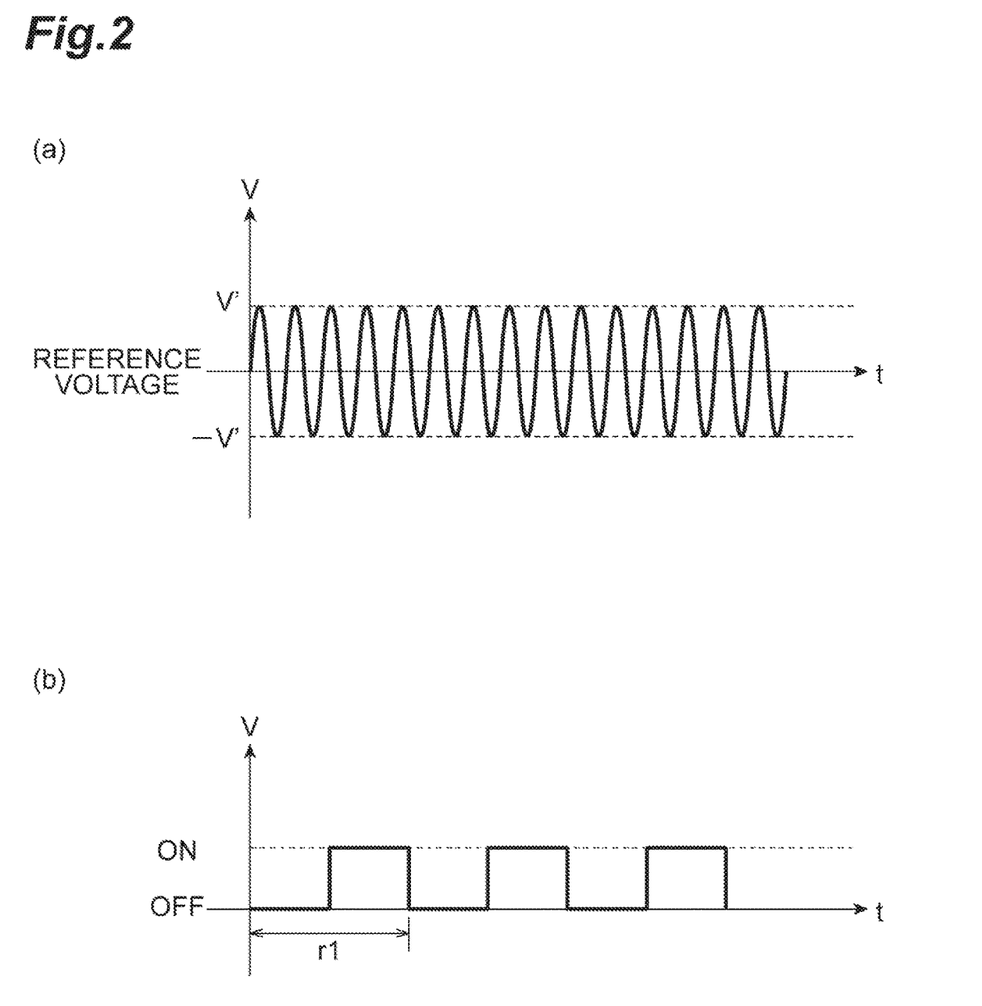
FIG. 2 is a diagram illustrating a waveform of a timing trigger signal.

The tester 11 applies an AC signal to the semiconductor device SD according to a timing trigger signal (a trigger signal) input from the processing unit 14. The AC signal is a signal of which a voltage periodically fluctuates between a predetermined positive and negative amplitude with respect to a reference voltage of the semiconductor device SD (see FIG. 2(a)). A period, a frequency, or an amplitude of the AC signal can be arbitrarily adjusted. Accordingly, since the voltage of the AC signal fluctuates to periodically increase or decrease with respect to the reference voltage of the semiconductor device SD, the voltage of the AC signal is adjusted so that the amounts of current flowing through both sides are equal. Further, if a short-circuited portion is included inside the semiconductor device SD, the short-circuited portion generates heat and becomes a heat source due to the applied AC signal. The timing trigger signal is a rectangular wave signal having a predetermined lock-in cycle r1 in a lock-in measurement (see FIG. 2(b)). The timing trigger signal periodically fluctuates between two values of on and off (see FIG. 2(b)).

The tester 11 applies an AC signal having an amplitude in an OFF period of a lock-in cycle that is smaller than in an ON period of the lock-in cycle to the semiconductor device SD. Specifically, the tester 11 sets the amplitude of the AC signal to 0 or a small value close to 0 in the OFF period of the lock-in cycle. In the following description, the amplitude of the AC signal in the OFF period of the lock-in cycle is assumed to be 0. Further, the tester 11 sets a frequency of the AC signal to be higher than a frequency of the timing trigger signal. Specifically, if the frequency of the timing trigger signal is F, M is an odd number and the frequency of the AC signal is F×(N+M)/N when the tester 11 waits for N arrivals of the timing trigger at a certain point. An upper limit of the frequency of the AC signal depends on the semiconductor device SD since the upper limit is determined by an upper limit at which the AC signal arrives at a heat source.

Even when the heat source position is near a bonding surface of a metal due to application of the AC signal from the tester 11 to the semiconductor device SD, a transfer of heat due to the Peltier effect can be suppressed (which will be described below in detail). Here, in the semiconductor device SD to which the AC signal is applied, infrared rays according to the AC signal are emitted from the heat source. A detection signal is output by the infrared camera 10 that has detected the infrared rays. Subsequently, an integration process is performed on the detection signal at a cycle (the lock-in cycle) of the timing trigger signal by the data analysis unit 15a, and a phase delay amount relative to the timing trigger signal is calculated for the detection signal after integration. The heat source position is identified from the phase delay amount by the data analysis unit 15a. When the detection signals are integrated, the AC signals included in the detection signal are similarly integrated. Therefore, when a phase difference between the AC signal applied from the tester 11 and the timing trigger signal having the lock-in cycle is always constant, the AC signal is greatly amplified after the integration. Accordingly, the value of the phase delay amount of the detection signal after the integration may change and accuracy in identifying the heat source position may be degraded.

Figure 3:
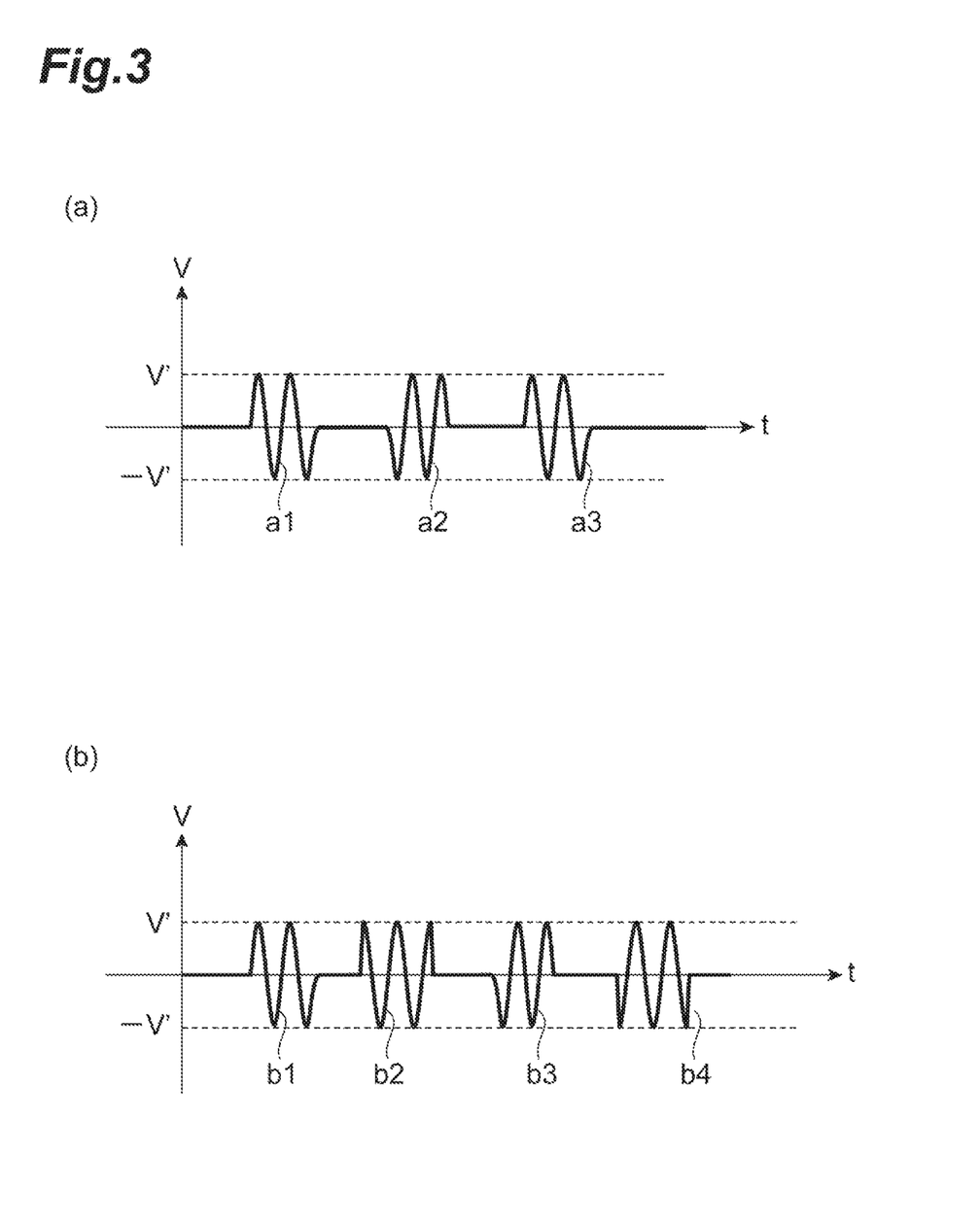
FIG. 3 is a diagram illustrating an example of a waveform of an AC signal.

Therefore, in this embodiment, when the AC signal included in detection signals with a plurality of lock-in cycles are integrated, the tester 11 changes a phase of the AC signal at each lock-in cycle so that the amplitude of the AC signal is canceled (preferably, completely canceled). For example, the phase may be changed by n° at each of the lock-in cycles (n is an arbitrary value except for 360 among aliquot parts of 360). More specifically, when the tester 11 applies an AC signal of which an amplitude has been modulated so that the amplitude is V' in the ON period of the lock-in cycle and 0 in the OFF period as illustrated in FIG. 3(a), the tester 11 adjusts the frequency of the AC signal so that the phase of the AC signal is changed by 180° every cycle. That is, the tester 11 adjusts the frequency of the AC signal so that a phase of an AC signal a2 in the ON period of a second cycle changes by 180° from a phase of an AC signal a1 in the ON period of a first cycle. Since the phase of the AC signal changes by 180° every cycle, a phase of an AC signal a3 in the ON period of a third cycle is the same as the phase of the AC signal a1 in the ON period of the first cycle. In this case, since the amplitude of the AC signal is canceled in two cycles, the amplitude of the AC signal can be canceled when the detection signals of the lock-in cycle are integrated.

Further, the tester 11 may adjust the frequency of the AC signal to change the phase of the AC signal by 90° every cycle, as illustrated in FIG. 3(b). In this case, a phase of an AC signal b2 in the ON period of a second cycle changes by 90° with respect to an AC signal b1 in the ON period of a first cycle, a phase of an AC signal b3 in the ON period of a third cycle changes by 90° with respect to the AC signal b2, and a phase of an AC signal b4 in the ON period of a fourth cycle changes by 90° with respect to the AC signal b3. In this case, since the amplitude of the AC signal is canceled in four cycles, the amplitude of the AC signal can be canceled when the AC signals of the lock-in cycle are integrated.

Figure 4:
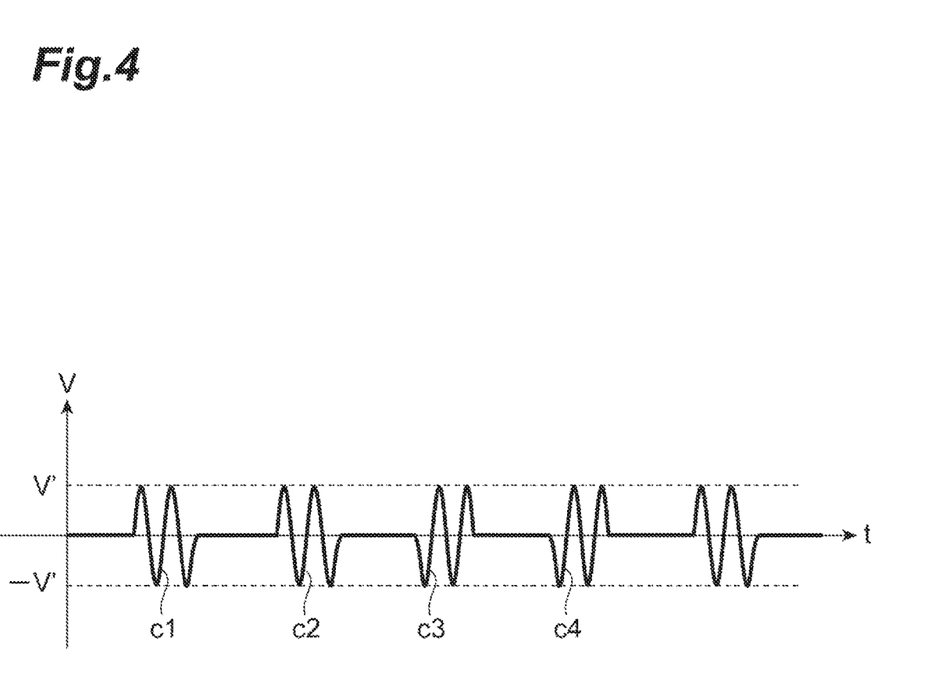
FIG. 4 is a diagram illustrating an example of a waveform of an AC signal.

Further, the tester 11 may adjust the frequency of the AC signal to change the phase of the AC signal by 180° every two cycles, as illustrated in FIG. 4.

In this case, an AC signal c1 in the ON period of a first cycle and an AC signal c2 in the ON period of a second cycle have the same phase. Both of an AC signal c3 in the ON period of a third cycle and an AC signal c4 in the ON period of a fourth cycle have a phase changed by 180° from the phase of the AC signals c1 and c2. In this case, since the amplitude of the AC signal is canceled in two cycles, the amplitude of the AC signal can be canceled when the AC signals of the lock-in cycle are integrated. A method of changing a phase is not limited to the above, and the phase may be changed by 180° every three or four cycles or the phase may be changed by 90° every two cycles so that the amplitudes of the integrated AC signal is eventually canceled.

Further, the amplitude of the integrated AC signal does not necessarily have to be completely canceled. For example, if adjustment is performed so that the phase of the AC signal is changed by 0° over 99 cycles of the lock-in cycle and the phase of the AC signal is changed by 180° over 100 cycles, the amplitude of the AC signal is not completely canceled at the time of integration, but since it is conceivable that the amplitude of the AC signal after integration is sufficiently negligible, the amplitude is allowed. That is, even when the amplitude is not completely canceled, the amplitude is allowed if the amplitude of the AC signal after integration is in an order of a measurement error.

Figure 5:
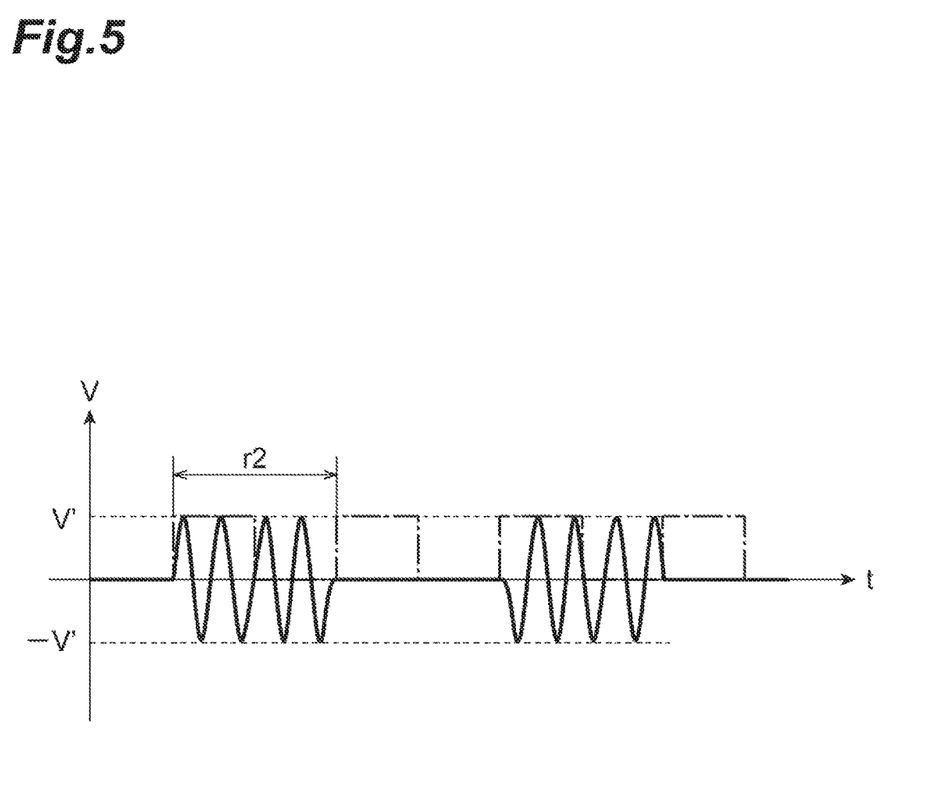
FIG. 5 is a diagram illustrating an example of a waveform of an AC signal in which a lock-in measurement is defective.

The tester 11 applies an AC signal in a range that does not deviate from the ON/OFF periods of the lock-in cycle so that the lock-in measurement is not incomplete. Therefore, even when the amplitude of the AC signal after integration is canceled, an AC signal having the same amplitude as in the ON period of the lock-in cycle r2 should not be applied in the OFF period of the lock-in cycle r2, as illustrated in FIG. 5.

Referring back to FIG. 1, the infrared camera 10 detects light output from the semiconductor device SD according to the AC signal, and outputs a detection signal. The infrared camera 10 detects (images) infrared rays from the heat source as the light output from the semiconductor device SD. More specifically, the infrared camera 10 detects black body radiation from the heat source. The detection signal output by the infrared camera 10 is a signal according to the detected infrared rays, that is, the amount of generated heat. Since the amount of generated heat changes over time according to a distance from the heat source (a distance in a depth direction of the semiconductor device SD), the detection signal is a signal corresponding to the distance from the heat source. The detection signal output from the infrared camera 10 is input to the processing unit 14.

The processing unit 14 outputs the timing trigger signal to the tester 11 and the data analysis unit 15a. Further, if the detection signal is input, the processing unit 14 outputs the detection signal to the data analysis unit 15a.

The computer 15 includes the data analysis unit 15a that identifies a heat source position of the semiconductor device SD based on the detection signal and the timing trigger signal, the condition setting unit 15c that sets the AC signal applied to the semiconductor device SD or the measurement position, and the control unit 15b that controls the infrared camera 10, the processing unit 14, the tester 11, and the stage 25. The display unit 28 that displays an analysis result or an image such as a pattern image of the semiconductor device SD or the input unit 29 that inputs an analysis condition is connected to the computer 15.

The condition setting unit 15c sets a condition (a frequency, amplitude, or the like) of the AC signal generated by the tester 11 or the timing trigger signal generated by the processing unit 14. Further, the condition setting unit 15c sets coordinates of the stage 25 in order to measure a desired position of the semiconductor device SD. Specifically, a user indicates coordinates using the input unit 29 while viewing the display unit 28 of the semiconductor device SD.

The control unit 15b controls the tester 11, the processing unit 14, and the stage 25 based on, for example, the condition of the AC signal or the coordinates set by the condition setting unit 15c.

The data analysis unit 15a integrates the detection signal input from the processing unit 14 at the cycle of the timing trigger signal (that is, the lock-in cycle). The data analysis unit 15a analyzes the heat source position of the semiconductor device SD based on the detection signal after integration. Here, among heat source positions, a two-dimensional position with no consideration of a depth of the heat source can be simply identified from the detection signal (the captured image) from the infrared camera 10. On the other hand, a position in the depth direction of the heat source is identified (analyzed) by deriving the phase delay amount of the detection signal relative to the timing trigger signal. Since a phase of the detection signal changes according to the heat source position (the depth of the heat source in the semiconductor device SD), the phase delay amount of the detection signal relative to the timing trigger signal also changes according to the heat source position. Specifically, the phase delay amount of the detection signal increases in proportion to the depth of the heat source in the semiconductor device SD.

The data analysis unit 15a obtains the depth of the heat source from the derived phase delay amount. More specifically, the data analysis unit 15a derives the depth of the heat source by multiplying the derived phase delay amount by a heat propagation velocity determined according to the semiconductor device SD. If v (m/s): heat propagation velocity, f (kHz): frequency of a modulation current, K (W/m/k): thermal conductivity of the semiconductor device SD, q (J/g/k): specific heat of the semiconductor device SD, and $\rho$ (kg/m$^{-3}$): density of the semiconductor device SD, the heat propagation velocity v can be obtained using Equation (1) below.

[Equation 1]

$$v = 2\pi\sqrt{f}\sqrt{\frac{K}{pq\pi}} \quad (1)$$

The data analysis unit 15a may store a table defining a correspondence relationship between the phase delay amount and the depth of the heat source in advance, and derive the depth of the heat source based on the derived phase delay amount and the table. Thus, the two-dimensional position and the position in the depth direction of the heat source are identified, and the heat source position in the semiconductor device SD is uniquely identified.

Next, an operation and effects of the analysis system 1 according to this embodiment will be described.

If a modulation current is applied to a measurement object (a semiconductor device) in which there is a failure portion (for example, a short-circuited portion), a heat source is generated in the failure portion. In the related art, a technology for identifying a failure portion by measuring heat generated by a heat source using an infrared camera and identifying a position of the heat source is known. Here, if a portion in which the heat source is generated is near a bonding surface of different metals, a heat transfer is caused between the different metals according to the modulation current by the Peltier effect, and the heat source may be measured as being in a position different from the failure portion.

Figure 6:
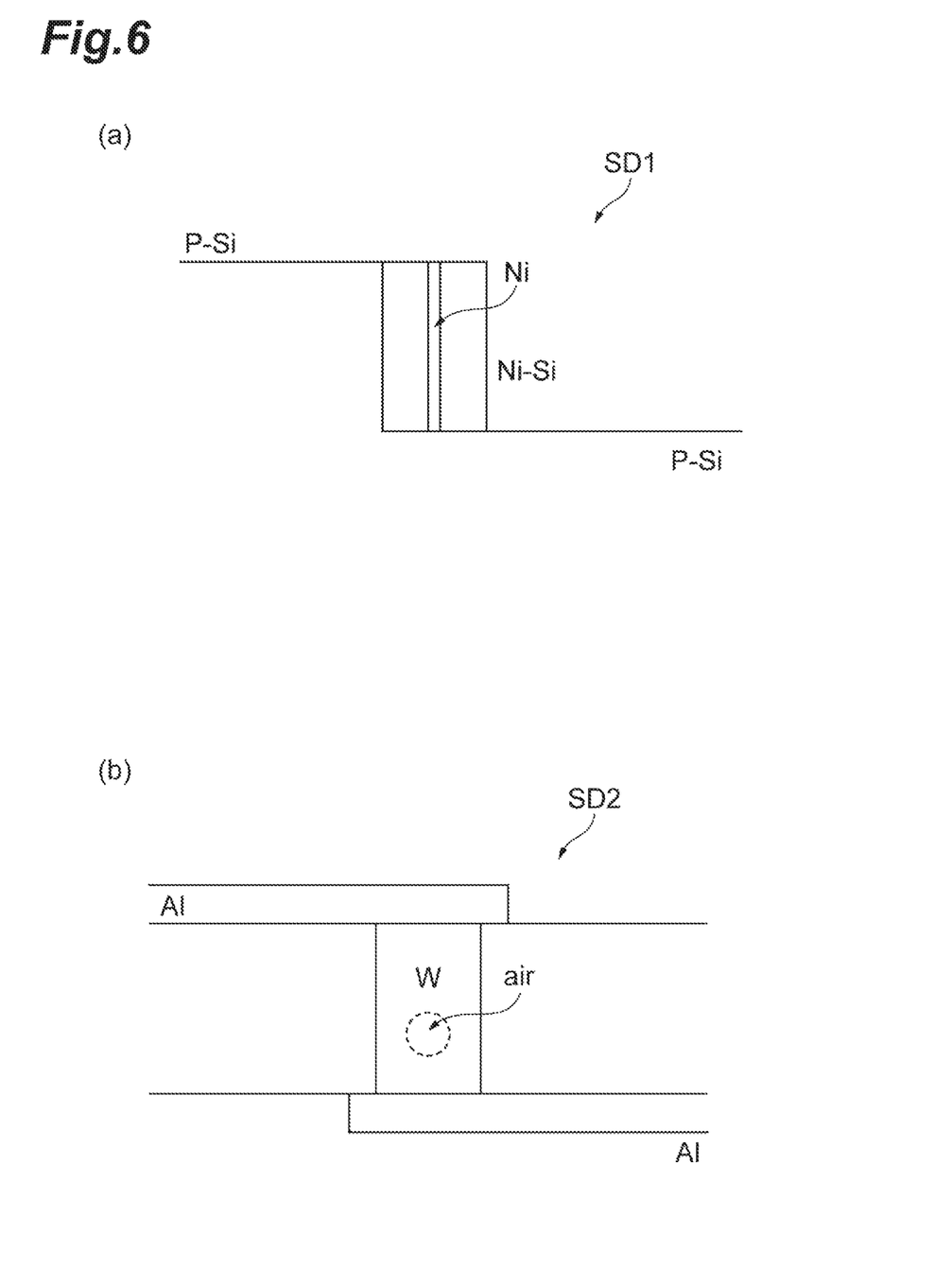
FIG. 6 is a diagram illustrating an example of a semiconductor device in which movement of a heat source by the Peltier effect occurs.

An example in which heat is transferred by the Peltier effect will be described with reference to FIG. 6. In a semiconductor device SD1 illustrated in FIG. 6(a), a nickel silicon layer Ni—Si is arranged between two polysilicon layers P—Si. When such a semiconductor device SD1 is created, nickel Ni may be precipitated from the nickel silicon layer Ni—Si. In this state, if a current flows through the semiconductor device SD1, a heat source is generated at a portion where the nickel Ni is precipitated. However, since a difference between Peltier coefficients of the nickel Ni and the polysilicon layer P—Si is equal to or greater than a certain value, an influence of the Peltier effect on the heat source appears and the heat is transferred.

Further, in a semiconductor device SD2 illustrated in FIG. 6(b), a through electrode formed of tungsten W is arranged in an integrated circuit of a through silicon electrode structure (TSV: Through-Silicon Via). In the semiconductor device SD2, aluminum Al wirings are formed at both ends of the through electrode. If air is added to the tungsten W at a time of forming the through electrode, a heat source is generated at a portion where the air is added when a current flows therethrough. In this case, since a difference between Peltier coefficients of the aluminum Al and the tungsten W is equal to or greater than a certain value, an influence of the Peltier effect on the heat source appears and the heat is transferred. Thus, there are various generation factors of the heat source, but if a heat source position is near a bonding surface of different metals, the heat is transferred by the Peltier effect.

In this regard, in the analysis system 1, since the AC signal is applied from the tester 11 to the semiconductor device SD, a direction of the current applied to the semiconductor device SD periodically changes (changes to an opposite direction). More specifically, since the AC signal is adjusted so that the amounts of current flowing through both sides are equal to the reference voltage of the semiconductor device SD, the influence of the Peltier effect is canceled and a situation in which heat is transferred to a position different from a failure portion can be suppressed. Since infrared rays from the semiconductor device SD change according to the heat source position, it is possible to appropriately identify the heat source position corresponding to the failure portion by analyzing the heat source position based on the infrared rays.

Further, the tester 11 applies an AC signal according to a timing trigger signal with a predetermined lock-in cycle and applies an AC signal with an amplitude in the OFF period of the lock-in cycle that is smaller than the ON period of the lock-in cycle. More preferably, the tester 11 sets the amplitude of the AC signal to 0 in the OFF period of the lock-in cycle. Accordingly, lock-in measurement can be appropriately performed according to the lock-in cycle.

Further, when the AC signals included in a detection signal with a plurality of lock-in cycles are integrated, the tester 11 changes a phase of the AC signal at each of the lock-in cycles so that the amplitude of the AC signal is canceled. Accordingly, it is possible to suppress a situation in which a result of identifying the heat source position is influenced by the integrated AC signal.

Further, the tester 11 causes the frequency of the AC signal to be higher than the frequency of the timing trigger signal. Accordingly, a direction of the current applied to the semiconductor device SD is frequently changed by the AC signal, and it is possible to further suppress the situation in which the heat is transferred by the Peltier effect.

Further, the data analysis unit 15a identifies the heat source position by deriving the phase delay amount of the detection signal relative to the timing trigger signal. The phase delay amount of the detection signal relative to the timing trigger signal changes according to infrared rays output from the semiconductor device SD. Therefore, it is possible to analyze the heat source position by deriving the phase delay amount of the detection signal. The derivation of the phase delay amount can be easily performed. Further, since the phase delay amount and the infrared rays output from the semiconductor device SD have a close correspondence relationship, it is possible to identify the heat source position easily and with high accuracy by deriving the phase delay amount of the detection signal.

Further, it is possible to appropriately detect light (infrared rays) with a simple configuration by using the infrared camera 10 that detects infrared rays from a heat source as light output from the semiconductor device SD.

Second Embodiment

Next, an analysis system 1A according to a second embodiment will be described with reference to FIG. 7. In the description of this embodiment, a difference between this embodiment and the first embodiment described above will be mainly described.

Figure 7:
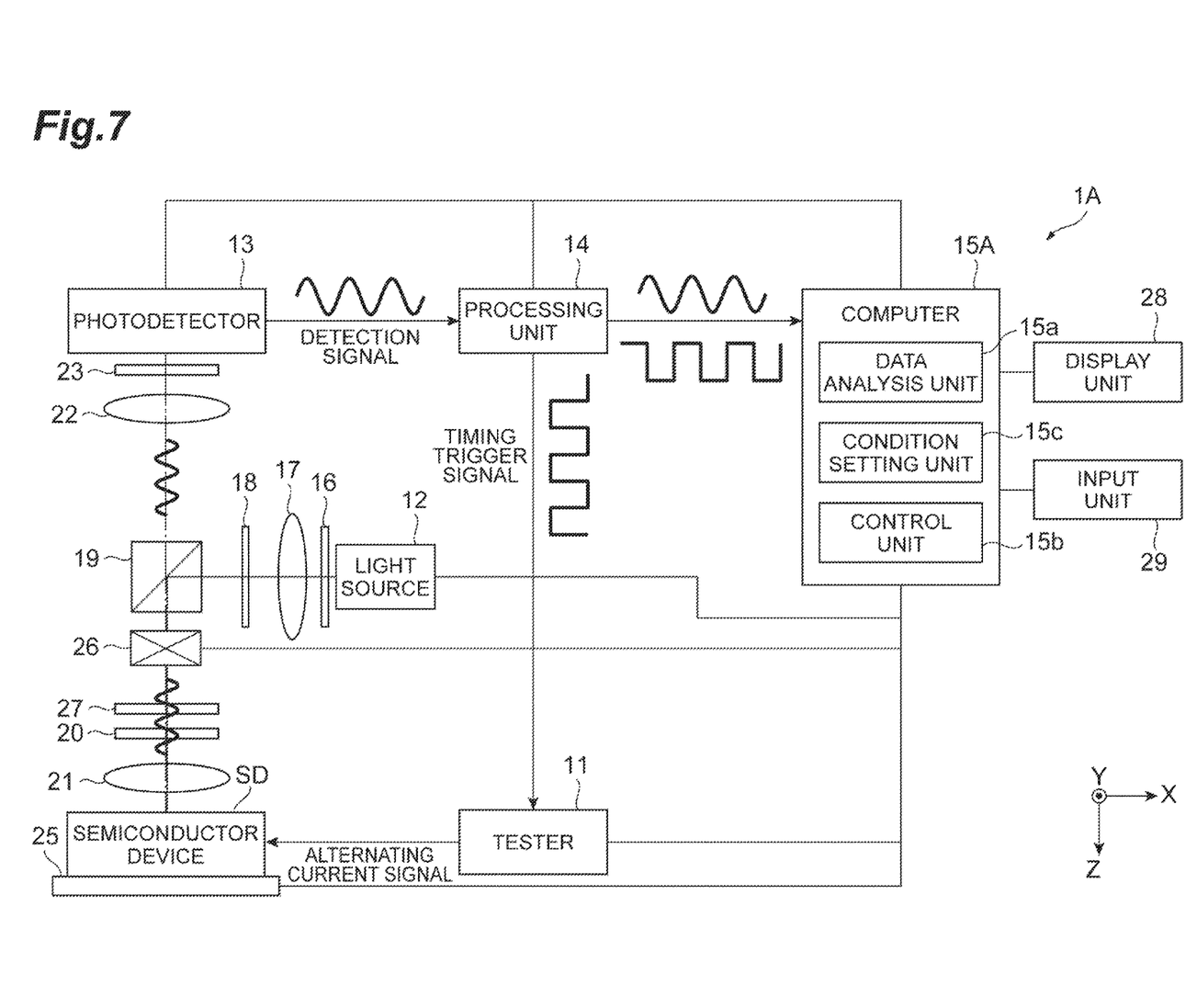
FIG. 7 is a configuration diagram of an analysis system according to a second embodiment of the present invention.

As illustrated in FIG. 7, in the analysis system 1A according to the second embodiment, reflected light from the semiconductor device SD is detected by the photodetector 13 (the light detection unit) rather than an infrared camera. Further, the analysis system 1A includes a light source 12 (a light irradiation unit) that irradiates the semiconductor device SD with light. Further, the analysis system 1A includes an optical scanner 26 that irradiates the set measurement point with light, and a short pass filter 27 that prevents infrared rays generated in the semiconductor device SD from being directed to the photodetector 13.

The light source 12 irradiates the semiconductor device SD with light (irradiated light). The light source 12 includes a super luminescent diode (SLD). The light source 12 may be, for example, a laser light source such as a laser diode (LD) or a light source using a light emitting diode (LED) or a lamp light source. Further, the irradiated light may be CW light or may be pulsed light. A wavelength of the irradiated light is, for example, about 1.3 µm, and a refractive index in the measurement object mainly formed of silicon is about 3.5.

The irradiated light output from the light source 12 is input to a polarizer 18 via a pinhole 16 and a lens 17. The polarizer 18 transmits only the radiation light polarized in a specific direction, and the irradiated light transmitted through the polarizer 18 is input to a polarization beam splitter (hereinafter referred to as a PBS) 19. The PBS 19 transmits the light polarized in a specific direction and reflects the light polarized in a specific direction. The PBS 19 reflects the irradiated light transmitted through the polarizer 18 toward the optical scanner 26. The optical scanner 26 is, for example, a galvano mirror scanner, a polygon mirror scanner, or the like, and is controlled so that a desired position of the semiconductor device SD is irradiated with the light from the PBS 19. The polarizer 18 may be omitted if the polarizer 18 is not necessary.

The irradiated light output from the optical scanner 26 passes through the short pass filter 27 and is radiated toward the semiconductor device SD via a λ/4 plate 20 and a lens 21. More specifically, the irradiated light is radiated toward a measurement point set for the semiconductor device SD.

Light (reflected light) reflected from the measurement point according to the irradiated light passes through the lens 21, the short pass filter 27 (an infrared ray shielding unit), the λ/4 plate 20, and the optical scanner 26 again and is input to the PBS 19. In this case, the short pass filter 27 can shield infrared rays generated in a measurement object MO. Further, since a polarization direction of the light input to the PBS 19 is tilted due to the light input to the PBS 19 being transmitted through the λ/4 plate 20 twice, the PBS 19 transmits the reflected light. The reflected light is input to the photodetector 13 via a lens 22 and a pinhole 23. Thus, for the optical system of this embodiment, a confocal optical system is used, and is configured so that reflected light from a limited focus range can be detected. Although the pinholes 16 and 23 are used in this embodiment, the confocal optical system may be realized using a difference in refractive index between a core and a cladding using an optical fiber.

The photodetector 13 detects the reflected light reflected from the semiconductor device SD according to the irradiated light. Further, the photodetector 13 converts the detected reflected light into a detection signal, which is an analog signal, and outputs the detection signal. The photodetector 13 is an avalanche photodiode (APD), a photodiode (PD), a photo multiplier tube (PMT), or the like. Here, in a state in which a heat source is generated, a material refractive index of the semiconductor device SD changes according to heat from the heat source, and a reflectance of the reflected light changes. Such a temporal change in the reflectance of the reflected light appears as a temporal change of the detection signal output from the photodetector 13. That is, the temporal change in the detection signal output from the photodetector 13 changes according to a speed of be thermal response that the measurement point receives from the heat source. Naturally, the speed of the thermal response that the measurement point receives from the heat source is higher as the measurement point nears the heat source. The detection signal output from the photodetector 13 is input to the processing unit 14. A process in the processing unit 14 is the same as that in the first embodiment.

A computer 15A includes the data analysis unit 15a that identifies a heat source position of the semiconductor device SD based on the detection signal and a timing trigger signal, the condition setting unit 15c that sets an AC signal to be applied to the semiconductor device SD or the measurement point, and the control unit 15b that controls the photodetector 13, the processing unit 14, the optical scanner 26, the tester 11, and the stage 25. Further, the display unit 28 that displays an analysis result or an image such as a pattern image of the semiconductor device SD and the input unit that inputs an analysis condition is also connected to the computer 15A.

The condition setting unit 15c sets a condition (a frequency, amplitude, or the like) of the AC signal generated by the tester 11 or the timing trigger signal generated by the processing unit 14. Further, the condition setting unit 15c sets the measurement point for the semiconductor device SD, and specifically, a user indicates at least one measurement point using the input unit 29 while viewing the display unit 28 on which the pattern image of the semiconductor device SD has been displayed. An example of the pattern image includes an LSM image. The condition setting unit 15c sets position information (an x coordinate and a y coordinate) on a surface of the measurement object MO based on position information of the indicated measurement point.

The control unit 15b controls the tester 11, the processing unit 14, and the optical scanner 26 based on the condition of the signal or the position information of the measurement point set by the condition setting unit 15c.

The data analysis unit 15a identifies the heat source position of the semiconductor device SD based on an integrated detection signal, as in the first embodiment. The data analysis unit 15a identifies the heat source position based on a derived distance from the measurement point to the heat source. More specifically, the data analysis unit 15a derives the phase delay amount of the detection signal and derives the distance from the measurement point to the heat source at each of three measurement points of the semiconductor device SD set by the condition setting unit 15c. Then, a three-dimensional heat source position is uniquely identified based on the distance to the heat source at each of the three measurement points.

If four or more measurement points are set, the data analysis unit 15a may perform measurement while narrowing down a region in which the heat source position exists. For example, the region in which the heat source position exists can be estimated by randomly setting four or more measurement points for the semiconductor device SD, deriving a distance between each of the measurement point and the heat source position, and comparing the distances. The data analysis unit 15a can identify the heat source position by resetting the measurement points in the estimated area, narrowing down the region in which a heat source region exists, and finally setting at least three measurement points. Further, if the data analysis unit 15a identifies, for example, the heat source position from phase delay amounts at the three measurement points, the data analysis unit 15a may analyze the heat source position by two-dimensionally mapping the phase delay amounts of the respective measurement points. In this case, for example, even when there are two or more points of heat sources, it is easy to visually recognize heat source positions thereof from a two-dimensional map.

In the analysis system 1A according to this embodiment, the AC is applied to the semiconductor device SD that is irradiated with light. In a state in which a heat source is generated by the AC, reflected light reflected from a measurement point according to the irradiated light is detected, and the detection signal is output. In the state in which the heat source is generated, a reflectance of the reflected light changes according to heat from the heat source. Since a thermal response to the heat source quickens in inverse proportion to the distance from the heat source, it is possible to estimate the distance from the measurement point to the heat source by analyzing the detection signal of the reflected light of which the reflectance changes over time according to the heat from the heat source. Thus, by identifying the heat source position using optical probing in which the detection signal according to the reflected light of the semiconductor device SD is analyzed, it is possible to improve time resolution. By improving the time resolution, it is possible to appropriately measure a thermal response and to improve analysis accuracy of the heat source position even when a thickness of the measurement object is small and a thermal response is quick. Specifically, if probe light intensity greater than or equal to a certain intensity can be ensured, the time resolution has sub-nanosecond accuracy and an error in identifying the heat source position can be 100 nm or less.

The preferred embodiments of the present invention have been described above, but the present invention is not limited to the above embodiments. For example, the processing unit 14 may not generate the trigger signal, and the tester 11 may generate the trigger signal together with the AC signal and output the trigger signal to the analysis unit 15a via the processing unit 14 while applying the AC signal according to the trigger signal to the semiconductor device SD. Further, the semiconductor device SD may be driven by the AC signal applied by the tester 11. For example, the infrared camera and the photodetector have been illustrated as the light detection unit, but the present invention is not limited thereto and the light detection unit may have another configuration having a function of detecting light from the measurement object.

REFERENCE SIGNS LIST 1, 1A: Analysis system
10: Infrared camera
11: Tester
12: Light source
13: Photodetector
15, 15A: Computer
15a: Data analysis unit
15c: Condition setting unit
SD: Semiconductor device

The invention claimed is:

1. An analysis system identifying a heat source position inside a measurement object, the analysis system comprising:
an applying unit configured to apply an AC signal to the measurement object;
a light detector configured to detect light from the measurement object according to the AC signal and outputting a detection signal; and
an analyzer configured to identify the heat source position based on the detection signal,
wherein the applying unit is configured to apply the AC signal with an amplitude in an OFF period of a lock-in cycle that is smaller than in an ON period of the lock-in cycle according to a trigger signal with a predetermined lock-in cycle.

2. The analysis system according to claim 1,
wherein the applying unit is configured to set the amplitude of the AC signal to 0 in the OFF period of the lock-in cycle.

3. The analysis system according to claim 1,
wherein the applying unit is configured to change a phase of the AC signal every lock-in cycle so that the amplitude of the AC signal is canceled when AC signals with a plurality of lock-in cycles are integrated.

4. The analysis system according to claim 1,
wherein the applying unit is configured to cause a frequency of the AC signal to be higher than a frequency of the trigger signal.

5. The analysis system according to claim 1,
wherein the analyzer is configured to identify the heat source position by deriving a phase delay amount of the detection signal relative to the trigger signal.

6. The analysis system according to claim 1,
wherein the light detector comprises an infrared camera that is configured to detect infrared rays from a heat source as the light from the measurement object.

7. The analysis system according to claim 1, further comprising:
a setting unit configured to set a measurement point for the measurement object; and
a light irradiator configured to irradiate the measurement object with light,
wherein the light detector comprises a photodetector detecting light reflected from the measurement point as the light from the measurement object.

8. An analysis method for identifying a heat source position inside a measurement object, the analysis method comprising:
applying an AC signal to the measurement object;
detecting light from the measurement object according to the AC signal and outputting a detection signal; and
identifying the heat source position based on the detection signal,
wherein applying the AC signal comprises applying the AC signal with an amplitude in an OFF period of a lock-in cycle that is smaller than in an ON period of the lock-in cycle according to a trigger signal with a predetermined lock-in cycle.

9. The analysis method according to claim 8,
wherein applying the AC signal comprises setting the amplitude of the AC signal to 0 in the OFF period of the lock-in cycle.

10. The analysis method according to claim 8,
wherein applying the AC signal comprises changing a phase of the AC signal every lock-in cycle so that the amplitude of the AC signal is canceled when AC signals with a plurality of lock-in cycles are integrated.

11. The analysis method according to claim 8,
wherein applying the AC signal comprises causing a frequency of the AC signal to be higher than a frequency of the trigger signal.

12. The analysis method according to claim 8,
wherein identifying the heat source position comprises identifying the heat source position by deriving a phase delay amount of the detection signal relative to the trigger signal.

\* \* \* \* \*